United States Patent [19]

Baker et al.

[11] 4,117,010
[45] Sep. 26, 1978

[54] THIOLCARBAMATE SULFOXIDES STABILIZED WITH HINDERED PHENOLS

[75] Inventors: Don R. Baker, Orinda; Francis H. Walker, Mill Valley, both of Calif.

[73] Assignee: Stauffer Chemical Company, Westport, Conn.

[21] Appl. No.: 721,247

[22] Filed: Sep. 8, 1976

[51] Int. Cl.² .................... C07C 147/14; A01N 9/14; C07C 155/02
[52] U.S. Cl. .................. 260/561 S; 71/103
[58] Field of Search ............ 260/551 R; 71/122, 103, 71/126

[56] References Cited

U.S. PATENT DOCUMENTS

| | | | |
|---|---|---|---|
| 1,628,035 | 5/1927 | Denny | 71/126 X |
| 2,110,842 | 3/1938 | Ressler | 71/126 |
| 3,928,436 | 12/1975 | Tilles et al. | 260/551 R |
| 3,975,180 | 8/1976 | Gozzo et al. | 260/551 R X |
| 4,008,071 | 2/1977 | Gozzo et al. | 260/553 R X |
| 4,025,487 | 5/1977 | Dexter et al. | 260/559 R X |

FOREIGN PATENT DOCUMENTS 47-23,434 3/1969 Japan .......................... 71/122

OTHER PUBLICATIONS

Kobayashi et al., CA 82: 139272b, (1975).
Gozzo et al., CA 82: 169773h, (1975).

*Primary Examiner*—Daniel E. Wyman
*Assistant Examiner*—Thomas A. Waltz
*Attorney, Agent, or Firm*—Edwin H. Baker

[57] ABSTRACT

The thermal stability of a herbicidal thiolcarbamate sulfoxide is improved by adding a stabilizing amount of a hindered phenol of the formula

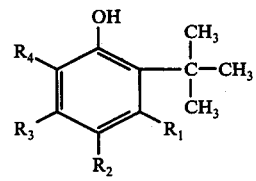

wherein $R_1$, $R_2$, $R_3$ and $R_4$ are independently selected from the group consisting of hydrogen, hydroxyl, lower alkyl and lower alkoxy.

23 Claims, No Drawings

THIOLCARBAMATE SULFOXIDES STABILIZED WITH HINDERED PHENOLS

This invention relates to stabilized thiolcarbamate sulfoxide compositions and to a method of improving the thermal stability of herbicidal thiolcarbamate sulfoxides.

DISCUSSION OF PRIOR ART

Thiolcarbamate sulfoxides of the type stabilized in accordance with the present invention are disclosed in U.S. Pat. Nos. 3,928,436 and 3,879,455, Belgian Pat. No. 805,839 and various other publications. While these compounds exhibit excellent herbicidal activity, they have been found to be somewhat thermally unstable. A study on the thermal stability of these compounds is reported in *The Journal of Chemistry and Industry*, Mar. 1, 1975, "On the Thermal and Chemical Stability of Carbamoyl Sulfoxides" by Gozzo, Masoero, Santi, Galluzzi and Barton. Belgian Pat. No. 829,971 to Montedison, describes crystalline carbamyl sulfoxide/urea adducts which have improved thermal stability compared to the corresponding sulfoxide.

SUMMARY OF THE INVENTION

It has now been found that the thermal stability of thiolcarbamate sulfoxides can be improved by combining the sulfoxide with a hindered phenol. Accordingly, this invention comprises a novel composition of matter comprising a thiolcarbamate sulfoxide of the formula

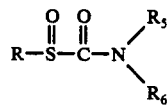

wherein R is selected from the group consisting of lower alkyl, halo lower alkyl, lower alkenyl, and alkoxy lower alkenyl; and $R_5$ and $R_6$ are independently selected from the group consisting of lower alkyl, cycloalkyl having 3-8 carbon atoms, alkylcycloalkyl, alkenyl, and alkynyl; and a stabilizing amount of a hindered phenol.

DETAILED DESCRIPTION OF THE INVENTION

The herbicidal thiolcarbamate sulfoxides stabilized in accordance with this invention are described and claimed in U.S. Pat. No. 3,928,436 to Harry Tilles and John E. Casida, issued Dec. 23, 1975. Typical compounds of this type are: S-ethyl-N,N-di-n-propyl carbamyl sulfoxide, S-ethyl-N,N-di-i-butyl carbamyl sulfoxide, S-n-propyl-N-n-butyl-N-ethyl carbamyl sulfoxide, S-ethyl-N-cyclohexyl-N-ethyl carbamyl sulfoxide, S-ethyl-N-methyl-N-α-methyl-propargyl carbamyl sulfoxide, S-n-propyl-N,N-di-n-propyl carbamyl sulfoxide, S-ethyl-N-allyl-N-n-propyl carbamyl sulfoxide, S-n-chloropropyl-N,N-diethyl carbamyl sulfoxide, S-ethoxyethenyl-N,N-di-n-propyl carbamyl sulfoxide, S-sec-butyl-N-methyl-N-cyclohexyl-methyl carbamyl sulfoxide and the like.

Hindered phenols that can be used are compounds having the formula

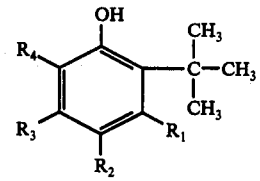

wherein $R_1$, $R_2$, $R_3$ and $R_4$ are independently selected from the group consisting of hydrogen, hydroxyl, lower alkyl and lower alkoxy. Illustrative examples of hindered phenols are 2,6-di-t-butyl phenol, 2,6-di-t-butyl-4-methyl phenol (butylated hydroxy toluene), 2,6-di-t-butyl-4-ethyl phenol, 2,6-di-t-butyl-4-hydroxy phenol, 2,4-di-t-butyl phenol, 2,4-di-t-butyl-5-hydroxy phenol (also known as 4,6-di-t-butyl resorcinol), 2,4-di-t-butyl-6-hydroxy phenol (also known as 3,5-di-t-butyl catechol), 2,4-di-t-butyl-6-methyl phenol, 2,4-di-t-butyl-5-methyl phenol, 2,6-di-t-butyl-4-methoxy phenol (butylated hydroxy anisole), 2,4-dimethyl-6-t-butyl phenol, 2,3-dimethyl-6-t-butyl phenol, 4-3thyl-6-t-butyl phenol, 2-t-butyl phenol, 2,4,6-tri-t-butyl phenol, 3-methyl-6-t-bu butyl phenol, 4-methyl-6-t-butyl phenol, and the like. The hindered phenols are well known compounds and are commercially available. Methods for preparation of hindered phenols are well known to one skilled in the art.

The term "lower alkyl" as used herein refers to straight or branched chain saturated aliphatic hydrocarbon groups of one to four carbon atoms, i.e., methyl, ethyl, propyl, i-propyl, n-butyl, s-butyl and t-butyl.

The term "lower alkoxy" as used herein refers to a straight or branched chain saturated aliphatic hydrocarbonoxy group containing one to four carbon atoms, i.e., methoxy, ethoxy, propoxy, i-propoxy, n-butoxy, i-butoxy, s-butoxy and t-butoxy.

The novel compositions of this invention contain a thiolcarbamate sulfoxide and a stabilizing amount of a hindered phenol. In general, the amount of hindered phenols required for effective stabilization of the sulfoxide is at least about 20% by weight, based on the weight of the sulfoxide. Preferably, the amount of hindered phenol added should be in the range of about 25% to about 300% by weight, and preferably about 50% to about 150% by weight based on the weight of the sulfoxide.

The following examples illustrate the improvement in thermal stability of thiolcarbamate sulfoxides by the addition of hindered phenols.

EXAMPLES

The stability of each of S-ethyl-N,N-di-n-propyl carbamyl sulfoxide, S-n-propyl-N,N-di-n-propyl carbamyl sulfoxide, and S-ethyl-N,N-di-isobutyl carbamyl sulfoxide alone and in combination with various hindered phenols was tested under side-by-side testing conditions. Into separate test tubes was placed an amount of sulfoxide and the designated hindered phenol was added. The quantities used in each test are specified in the following table. The test tubes were placed in a constant temperature oil bath maintained at 60° C. and each connected to a manometer. Thermal decomposition of the sulfoxide was determined by measurement of the gas evolved over a period of about 8 hours. The amount of gas evolved by each composition was measured as the displacement in centimeters (cm) of the oil in the manometer. The results of these tests are shown in the following table.

TABLE I

| Sulfoxide | grams | Hindered Phenol | grams | Gas Evolved (cm) |
|---|---|---|---|---|
| EXAMPLE NO. 1 | | | | |
| S-ethyl-N,N-di-n-propyl carbamyl sulfoxide | (1.0) | 2,6-di-t-butyl phenol | (1.0) | 1.9 |
| S-ethyl-N,N-di-n-propyl carbamyl sulfoxide | (1.0) | none | | 3.5 |
| EXAMPLE NO. 2 | | | | |
| S-ethyl-N,N-di-n-propyl carbamyl sulfoxide | (0.4) | butylated hydroxy anisole | (0.3) | 1.7 |
| S-ethyl-N,N-di-n-propyl carbamyl sulfoxide | (0.4) | 2,4-dimethyl-6-t-butyl phenol | (0.3) | 2.6 |
| S-ethyl-N,N-di-n-propyl carbamyl sulfoxide | (0.4) | none | | 3.2 |
| EXAMPLE NO. 3 | | | | |
| S-ethyl-N,N-di-n-propyl carbamyl sulfoxide | (0.5) | 2,4-di-t-butyl-3-methyl phenol | (0.5) | 0.7 |
| S-ethyl-N,N-di-n-propyl carbamyl sulfoxide | (0.5) | 2,4-di-t-butyl-3-methyl phenol | (0.3) | 2.0 |
| S-ethyl-N,N-di-n-propyl carbamyl sulfoxide | (0.5) | 2,4-di-t-butyl-3-methyl phenol | (0.1) | 4.2 |
| S-ethyl-N,N-di-n-propyl carbamyl sulfoxide | (0.5) | none | | 6.3 |
| EXAMPLE NO. 4 | | | | |
| S-ethyl-N,N-di-n-propyl carbamyl sulfoxide | (0.5) | 2,4,6-tri-t-butyl phenol | (0.5) | 1.6 |
| S-ethyl-N,N-di-n-propyl carbamyl sulfoxide | (0.5) | none | | 5.7 |
| EXAMPLE NO. 5 | | | | |
| S-ethyl-N,N-di-n-propyl carbamyl sulfoxide | (0.5) | 2,6-di-t-butyl phenol | (0.5) | 2.3 |
| S-ethyl-N,N-di-t-propyl carbamyl sulfoxide | (0.5) | 4,6-di-t-butyl-3-methyl phenol | (0.5) | 1.6 |
| S-ethyl-N,N-di-t-propyl carbamyl sulfoxide | (0.5) | none | | 6.3 |
| EXAMPLE NO. 6 | | | | |
| S-n-propyl-N,N-di-n-propyl carbamyl sulfoxide | (0.4) | butylated hydroxy anisole | (0.3) | 2.2 |
| S-n-propyl-N,N-di-n-propyl carbamyl sulfoxide | (0.4) | 2,4-dimethyl-6-t-butyl phenol | (0.3) | 2.1 |
| S-n-propyl-N,N-di-n-propyl carbamyl sulfoxide | (0.4) | none | | 3.2 |
| EXAMPLE NO. 7 | | | | |
| S-ethyl-N,N-di-isobutyl carbamyl sulfoxide | (0.6) | 2,6-di-t-butyl phenol | (0.5) | 2.3 |
| S-ethyl-N,N-isobutyl carbamyl sulfoxide | (0.6) | 4,6-di-t-butyl-3-methyl phenol | (0.5) | 1.9 |
| S-ethyl-N,N-di-isobutyl carbamyl sulfoxide | (0.6) | none | | 5.5 |
| EXAMPLE NO. 8 | | | | |
| S-n-propyl-N,N-di-n-propyl carbamyl sulfoxide | (0.5) | 2,6-di-t-butyl phenol | (0.5) | 1.8 |
| S-n-propyl-N,N-di-n-propyl carbamyl sulfoxide | (0.5) | 4,6-di-t-butyl-3-methyl phenol | (0.5) | 2.0 |
| S-n-propyl-N,N-di-n-propyl carbamyl sulfoxide | (0.5) | none | | 5.4 |
| EXAMPLE NO. 9 | | | | |
| S-ethyl-N,N-di-n-propyl carbamyl sulfoxide | (0.5) | 3,4-di-t-butyl-cathcol | (0.5) | 1.8 |
| S-ethyl-N,N-di-n-propyl carbamyl sulfoxide | (0.5) | none | | 5.7 |
| S-n-propyl-N,N-di-n-propyl carbamyl sulfoxide | (0.5) | 3,5-di-t-butyl catechol | (0.5) | 3.4 |
| S-n-propyl-N,N-di-n-propyl carbamyl sulfoxide | (0.5) | none | | 5.2 |
| S-ethyl-N,N-di-n-propyl carbamyl sulfoxide | (0.6) | 3,5-di-t-butyl catechol | (0.5) | 1.0 |
| S-ethyl-N,N-di-n-propyl carbamyl sulfoxide | (0.6) | none | | 4.4 |
| EXAMPLE NO. 10 | | | | |
| S-ethyl-N,N-di-n-propyl carbamyl sulfoxide | (0.5) | butylated hydroxytoluene | (0.5) | 2.6 |
| S-ethyl-N,N-di-n-propyl carbamyl sulfoxide | (0.5) | 4,6-di-t-butyl resorcinol | (0.5) | 2.1 |
| S-ethyl-N,N-di-n-propyl carbamyl sulfoxide | (0.5) | none | | 4.7 |
| S-n-propyl-N,N-di-n-propyl carbamyl sulfoxide | (0.5) | butylated hydroxytoluene | (0.5) | 2.5 |
| S-n-propyl-N,N-di-n-propyl carbamyl sulfoxide | (0.5) | 4,6-di-t-butyl resorcinol | (0.5) | 3.1 |
| S-n-propyl-N,N-di-n-propyl carbamyl sulfoxide | (0.5) | none | | 5.9 |
| S-ethyl-N,N-di-isobutyl carbamyl sulfoxide | (0.6) | butylated hydroxytoluene | (0.5) | 2.1 |
| S-ethyl-N,N-di-isobutyl carbamyl sulfoxide | (0.6) | 4,6-di-t-butyl resorcinol | (0.5) | 3.3 |
| S-ethyl-N,N-di-isobutyl carbamyl sulfoxide | (0.6) | none | | 3.6 |

The hindered phenol can be admixed with the herbicidal thiolcarbamate sulfoxide in any conventional manner to form a stabilized herbicidal composition.

The herbicidal compositions of this invention are generally applied to soil to control the growth of undesirable vegetation in the form of formulations containing the composition and an inert carrier. Herbicidal formulations generally take the form of dusts, wettable powders, granules, solutions, or emulsifiable concentrates.

Dusts are free-flowing powder compositions containing the herbicidal composition impregnated on a particulate carrier. The particle size of the carrier is usually in the range of from about 30 to 50 microns. Examples of suitable carriers are talc, bentonite, diatomaceous earth, and pryrophyllite. Anticaking and antistatic agents can be added, if desired. The composition generally contains up to 50% of active ingredient.

Wettable powders are finely divided compositions comprising a particulate carrier impregnated with the herbicidal composition and additionally containing one or more surface active agents. The surface agent promotes rapid dispersion of the powder in aqueous medium to form stable, sprayable suspensions. A wide variety of surface active agents can be used, for example, long chain fatty alcohols and alkali metal salts of sulfated fatty alcohols; salts of sulfonic acid; and esters of long chain fatty acids. A list of surface active agents suitable for use in agriculture formulations can be found in *Pesticide Formulations* by Wade Van Valkenburg, Marcel Dekker, Inc., N.Y. 1973 at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, and the like.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emsulsion of oil droplets. The emulsifiers used are usually a mixture of anionic and nonionic surfactants. Other additives such as spreading agents and stickers can be included in the emulsifiable concentrate if desired.

The compositions are applied to the soil to control the growth of undesirable vegetation at a rate to provide about 0.5 to about 50 pounds per acre, and preferably about 1 to about 20 pounds per acre, of active herbicidal ingredient. The amount of active ingredient used per acre will depend on overall cost and desired result.

What is claimed is:

1. A composition comprising a herbicidal thiolcarbamate sulfoxide and a stabilizing amount of a hindered phenol of the formula

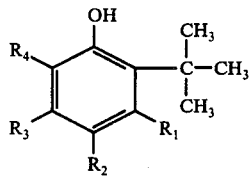

wherein $R_1$, $R_2$, $R_3$ and $R_4$ are independently selected from the group consisting of hydrogen, hydroxyl, lower alkyl and lower alkoxy.

2. The composition of claim 1 wherein said thiolcarbamate sulfoxide is a thiolcarbamate sulfoxide of the formula

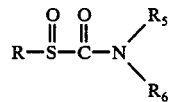

wherein R is selected from the group consisting of lower alkyl, halo lower alkyl, lower alkenyl, and alkoxy lower alkenyl; and $R_5$ and $R_6$ are independently selected from the group consisting of lower alkyl, cycloalkyl having 3–8 carbon atoms, alkylcycloalkyl, alkenyl, and alkynyl.

3. The composition of claim 1 wherein said thiolcarbamate sulfoxide is S-ethyl-N,N-di-n-propyl carbamyl sulfoxide.

4. The composition of claim 3 wherein said hindered phenol is 2,6-di-t-butyl phenol.

5. The composition of claim 3 wherein said hindered phenol is butylated hydroxy anisole.

6. The composition of claim 3 wherein said hindered phenol is 2,4-dimethyl-6-t-butyl phenol.

7. The composition of claim 3 wherein said hindered phenol is 2,4-di-t-butyl-3-methyl phenol.

8. The composition of claim 3 wherein said hindered phenol is 2,4,6-tri-t-butyl phenol.

9. The composition of claim 3 wherein said hindered phenol is 4,6-di-t-butyl-3-methyl phenol.

10. The composition of claim 3 wherein said hindered phenol is 3,5-di-t-butyl catechol.

11. The composition of claim 3 wherein said hindered phenol is 4,6-di-t-butyl resorcinol.

12. The composition of claim 1 wherein said thiolcarbamate sulfoxide is S-n-propyl-N,N-di-n-propyl carbamyl sulfoxide.

13. The composition of claim 12 wherein said hindered phenol is 2,6-di-t-butyl phenol.

14. The composition of claim 12 wherein said hindered phenol is 4,6-di-t-butyl-3-methyl phenol.

15. The composition of claim 12 wherein said hindered phenol is butylated hydroxy anisole.

16. The composition of claim 12 wherein said hindered phenol is 2,4-dimethyl-6-t-butyl phenol.

17. The composition of claim 12 wherein said hindered phenol is 3,5-di-t-butyl catechol.

18. The composition of claim 12 wherein said hindered phenol is 4,6-di-t-butyl resorcinol.

19. The composition of claim 1 wherein said thiolcarbamate sulfoxide is S-ethyl-N,N-di-isobutyl carbamyl sulfoxide.

20. The composition of claim 19 wherein said hindered phenol is 2,6-di-t-butyl phenol.

21. The composition of claim 19 wherein said hindered phenol is 4,6-di-t-butyl-3-methyl phenol.

22. The composition of claim 19 wherein said hindered phenol is 3,5-di-t-butyl catechol.

23. The composition of claim 19 wherein said hindered phenol is 4,6-di-t-butyl resorcinol.

* * * * *

UNITED STATES PATENT AND TRADEMARK OFFICE
CERTIFICATE OF CORRECTION

PATENT NO. : 4,117,010
DATED : September 26, 1978
INVENTOR(S) : Don R. Baker et al.

It is certified that error appears in the above–identified patent and that said Letters Patent are hereby corrected as shown below:

Column 3, Table I, Example No. 5, line 2, should read:

"S-ethyl-N,N-di-n-propyl carbamyl sulfoxide"

Column 3, Table I, Example No. 5, line 3, should read:

"S-ethyl-N,N-di-n-propyl carbamyl sulfoxide"

Column 3, Table I, Example No. 6, line 2, should read:

"S-n-propyl-N,N-di-n-propyl carbamyl sulfoxide"

Column 3, Table I, Example No. 7, line 2, should read:

"S-ethyl-N,N-di-isobutyl carbamyl sulfoxide"

Signed and Sealed this

Eleventh Day of September 1979

[SEAL]

Attest:

LUTRELLE F. PARKER
Attesting Officer   Acting Commissioner of Patents and Trademarks